United States Patent [19]

Kurtz

[11] Patent Number: 4,481,008
[45] Date of Patent: Nov. 6, 1984

[54] APPARATUS AND METHOD FOR RELIEVING EXCESS NEGATIVITY IN A DRAINAGE DEVICE

[75] Inventor: Leonard D. Kurtz, Woodmere, N.Y.
[73] Assignee: BioResearch Inc., Farmingdale, N.Y.
[21] Appl. No.: 309,796
[22] Filed: Oct. 8, 1981
[51] Int. Cl.³ ............................................ A61M 1/00
[52] U.S. Cl. ........................... 604/118; 604/319
[58] Field of Search ............... 128/274, 276, 218 NV, 128/347, 214.2, 765; 137/543.21, 540; 604/50, 51, 236, 237, 238, 317, 319, 118, 119, 320–323

[56] References Cited

U.S. PATENT DOCUMENTS

| | | | |
|---|---|---|---|
| 654,552 | 7/1900 | Morris | 137/543.21 |
| 2,374,368 | 4/1945 | Mejia | 128/218 NV |
| 2,538,662 | 1/1951 | Abbott | 128/274 |
| 3,245,429 | 4/1966 | Bacino et al. | 137/543.21 |
| 3,515,127 | 6/1970 | Reymond | 128/214.2 |
| 3,557,778 | 1/1971 | Hughes | 604/236 |
| 3,580,275 | 5/1971 | Hanson | 137/540 |
| 3,848,579 | 11/1974 | Real | 128/276 |
| 4,051,971 | 10/1977 | Saleri et al. | 128/276 |
| 4,105,031 | 8/1978 | Kurtz et al. | 128/276 |
| 4,289,158 | 9/1981 | Nehring | 137/205 |

Primary Examiner—C. Fred Rosenbaum
Assistant Examiner—J. L. Kruter
Attorney, Agent, or Firm—Larson and Taylor

[57] ABSTRACT

An apparatus and method for relieving high or excess negativity in an underwater drainage device is disclosed. The apparatus includes a syringe needle with a valve operatively connected to the syringe needle. The valve provides a sealed passageway from the atmosphere through the syringe needle and a spring urges the valve to a closed position except when high or excess negativity occurs in the underwater drainage device. In the method, the syringe needle pierces a resealable portion of the drainage device and a valve is provided in fluid communication with the syringe needle. After excess negativity is relieved, the syringe is removed from the resealable portion of the drainage device.

7 Claims, 4 Drawing Figures

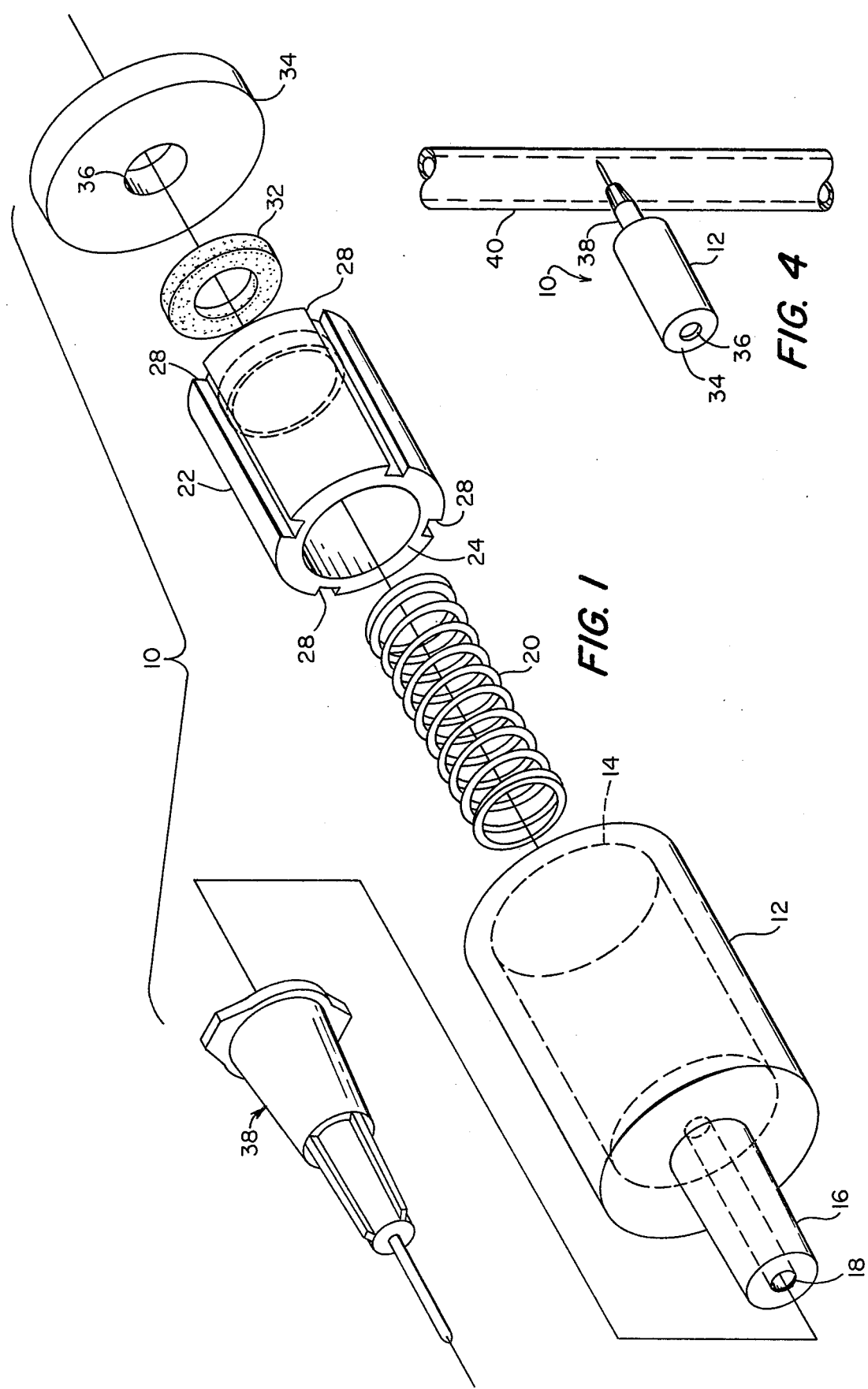

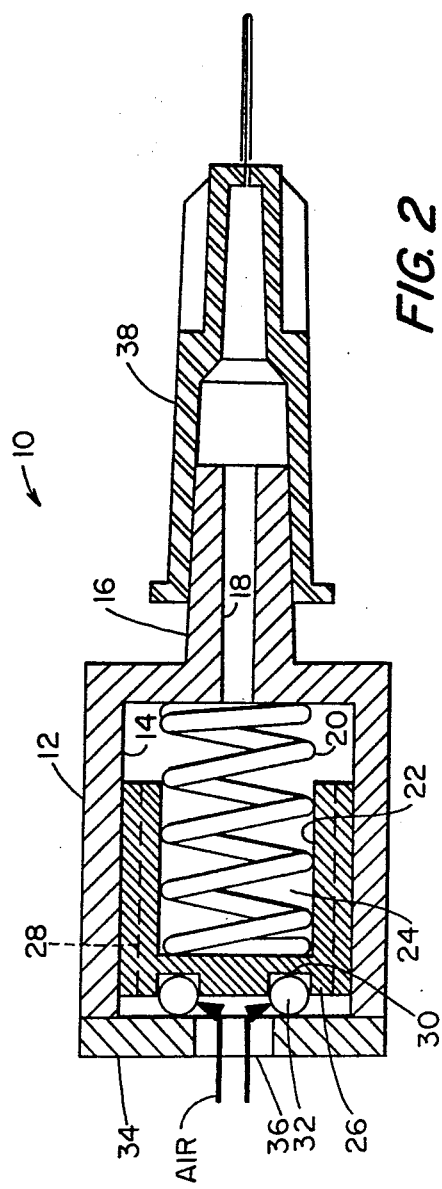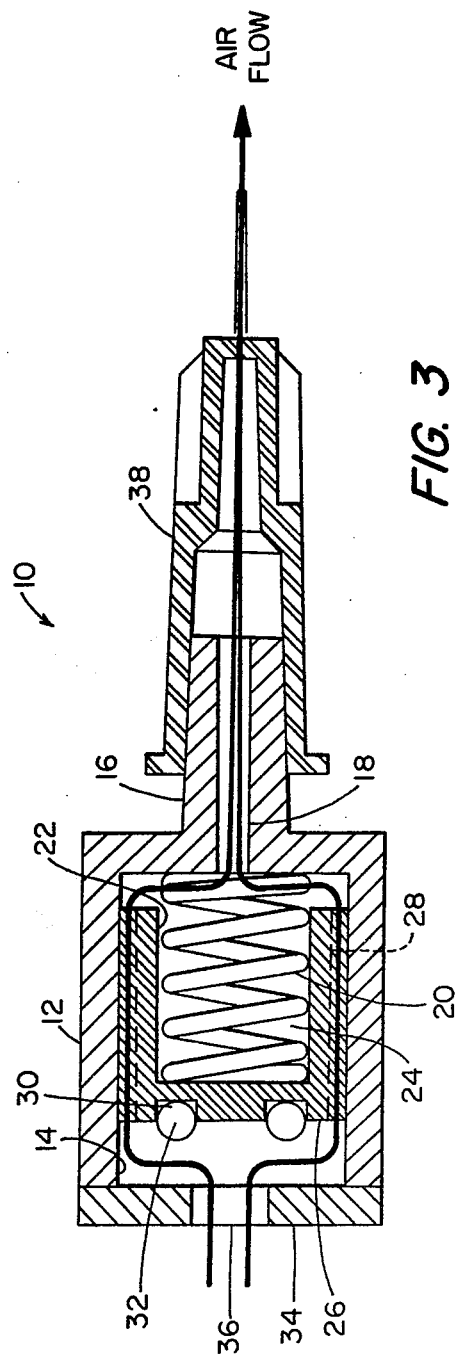

APPARATUS AND METHOD FOR RELIEVING EXCESS NEGATIVITY IN A DRAINAGE DEVICE

FIELD OF THE INVENTION

This invention relates to a surgical underwater drainage system used in draining fluids from the body, e.g. the pleural cavity, and is particularly concerned with an automatic device and method which relieves excess negativity within the body cavity.

BACKGROUND OF THE INVENTION

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the rib cage or such as occur, for example, where the patient has pleurisy, generates fluids in the pleural cavity which tend to obstruct normal breathing. It is necessary to provide a device which can remove these fluids from the pleural cavity and at the same time ensure that the desired degree of negative pressure is maintained within the pleural cavity.

One of the basic types of apparatus which have been used for this purpose is shown, for example, in U.S. Pat. Nos. 3,363,626 and 3,363,627, which are herein incorporated by reference. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity. However, such an apparatus required prefilling the underwater seal chamber with water and also prefilling the pressure manometer chamber to the desired level to maintain the desired degree of negativity within the pleural cavity.

In order to avoid the necessity and problems of having to prefill chambers in a drainage device, the underwater seal chamber is located at the lower end of the thorocotomy tube. In this manner, the underwater seal is formed by liquid drained from the patient's pleural cavity. Drainage systems of this nature and disclosed in U.S. Pat. No. 4,105,603 and application Ser. Nos. 107,329 and 120,295, which are herein incorporated by reference.

It has been found that doctors frequently will "milk" the thoracotomy tubes in an effort to remove any clots or obstructions from the tube. This milking of the tube is achieved by squeezing the flexible thoracotomy tube adjacent the upper end and drawing the fingers down the tube to cause the fluids within the tube to be passed out the lower end of the tube. Obviously, this action has the effect of substantially lowering the degree of negativity within the pleural cavity. Such high negativity can be damaging to the pleural cavity and may also cause the liquid within the underwater seal chamber to be drawn up into the pleural cavity. In addition, even with a surgical drainage device having a separate underwater seal chamber, the entire seal can be lost during periods of high negativity in the pleural cavity. The loss of the water seal has the potential for serious damage in the event that the suction becomes disconnected. Thus, there is need for a means for providing instant relief for the condition of excess negativity in the pleural cavity.

In applicant's pending U.S. application Ser. No. 256,152, a metered air pump is disclosed by which excess negative pressure can be relieved by pumping as many small units of air into the thoracotomy tube as necessary. However, relief is only provided upon actuation of the device by an attendant or the like and thus does not operate automatically.

SUMMARY OF THE INVENTION

The present invention provides a surgical underwater drainage device which overcomes the problems noted above with respect to prior art devices and provides an underwater drainage apparatus in which high or excess negativity can be automatically relieved. Furthermore, the system provided assures that the excess negativity is relieved slowly so that desired negativity is not lost. A method for relieving excess negativity is also provided.

According to the present invention, there is provided a surgical underwater drainage apparatus having a collection chamber with an underwater seal. Preferably, the underwater seal is located adjacent the lower end of the thoracotomy tube. Thus, when the thoracotomy tube is attached to the pleural cavity, liquid drained into the thoracotomy tube passes into the underwater seal chamber and forms the underwater seal. When the seal chamber is filled, the liquid overflows into the collection chamber.

There is further provided a negative pressure relief valve which is fluidly connected to the thoracotomy tube. This negative pressure relief valve is designed to bleed air to the thoracotomy tube during periods of excess negativity therein. During normal operation of the drainage device, the negative pressure relief valve does not permit the passage of any air into the thoracotomy tube. However, when excess negativity in the thoracotomy tube occurs, the negative pressure relief valve acts to bleed air to the thoracotomy tube. The negative pressure relief valve is actuated to bleed air as often as excess negativity occurs. Actuation of the negative pressure relief valve is stopped as soon as the excess negativity condition is relieved so that the desired negativity is maintained in the thoracotomy tube and drainage device.

In a preferred embodiment of the present invention, the negative pressure relief valve includes a spring based slidable valve sealed by an O-ring which opens to admit air when excess negativity occurs. The negative pressure relief valve also includes a syringe needle in fluid communication with the sealed side of the valve so that the relief valve is easily connected to the drainage device and preferably to the thoracotomy tube. In the preferred embodiment, the relief valve bleeds air into the thoracotomy tube whenever the pressure in the tube is less than $-20$ cm. of water.

In a preferred method of the present invention, whenever excess negativity occurs in a drainage device, the needle of the negative pressure relief valve is used to pierce the thoractomy tube or other resealable portion of the drainage device itself so that the valve can bleed air into the drainage device.

Additional features and advantages of the present invention will be apparent from a consideration of the following detailed description of the preferred embodiment of the invention in connection with the accompanying drawings.

BRIEF DESCRIPTION OF THE DRAWINGS

FIG. 1 is an exploded perspective view of the negative pressure relief valve of the present invention.

FIG. 2 is a cross-sectional side view of the negative pressure relief valve depicted in FIG. 1 in the closed position.

FIG. 3 is a cross-sectional side view of the negative pressure relief valve depicted in FIG. 1 in the open position.

FIG. 4 is a perspective view of the negative pressure relief valve depicted in FIG. 1 piercing the thoracotomy tube of a drainage device.

DETAILED DESCRIPTION OF THE PREFERRED EMBODIMENT

With reference now to the drawings in which like numerals represent like elements throughout the several views, a presently preferred embodiment of an excess negative pressure relief valve 10 is depicted in FIGS. 1 to 4. As shown, relief valve 10 has a valve housing 12 having a cylindrical cavity 14 therein. Located at one end of valve housing 12 is a tapered end 16 having a passageway 18 therethrough. Inside of cylindrical cavity 14 is a spring 20 biased against a slidable valve 22. As best shown in FIG. 1, slidable valve 22 has a cylindrical cavity 24 and an end member 26. Located around the periphery of slidable valve 22 are a plurality of channels 28 extending from end member 26 to the opposite end of slidable valve 22. Located on the opposite side of end member 26 from spring 20 is a circular recess 30 in end member 26 in which an O-ring 32 is received. Spring 20, slidable valve 22, and O-ring 32 are received in cylindrical cavity 14 of valve housing 12 as shown in FIGS. 2 and 3. Attached to the end walls of valve housing 12 to seal cylindrical cavity 14 from the atmosphere is a housing cap 34. Housing cap 34 includes an aperture 36 which is located coaxially with O-ring 32 and is sized to be smaller than O-ring 32.

Received on tapered end 16 is a standard syringe needle 38 having a 22 gauge needle, for example. Syringe needle 38 is sealingly received on tapered end 16 by a Luer Lock or other reliable syringe lock. As shown, syringe needle 38 is simply pressed fit onto tapered end 16.

Operation of negative pressure relief valve 10 to relieve excess or high negativity in a drainage device is accomplished in the following manner. Initially, negative pressure relief valve 10 is provided in the assembled form as shown in FIG. 2. Syringe needle 38 is then used to puncture a resealable portion of the underwater drainage apparatus. Conveniently, syringe needle 38 can puncture the rubber thoracotomy tube 40. However, a separate rubber diaphragm can be provided on the underwater drainage device to receive syringe needle 38. After excess or high negativity has been relieved, negative pressure relief valve 10 is easily removed by withdrawing syringe needle 38 from the resealable portion of the underwater drainage device.

The operation of negative pressure relief valve 10 when it is attached to the underwater drainage device is depicted in FIGS. 2 and 3. In FIG. 2, negative pressure relief valve 10 is depicted in the ready position. In this position, spring 20 presses against the bottom of valve housing 10 and end member 26. This causes O-ring 32 to press against housing cap 34. O-ring 32 thus seals cylindrical cavity 14 and the underwater drainage device from the inadvertent entry of atmospheric air into the drainage device.

When a high or excess negativity occurs in the drainage device, negative pressure relief valve 10 assumes the operating position shown in FIG. 3. In this position, the negative pressure in the drainage device has reduced the pressure within cylindrical cavity 14 to the point where atmospheric pressure is sufficient to push slidable valve 22 against spring 20. This causes O-ring 32 to disengage housing cap 34. As soon as this happens, atmospheric air passes through aperture 36 and around slidable valve 22 along channels 28. After passing sliding valve 22, the air continues through passageway 18, into syringe needle 38, and finally into the underwater drainage device. Although the movement of slidable valve 22 allows a relatively large volume of air to pass through passageway 18, it should be noted that the relatively small size of syringe needle 38 acts as a throttling or bleeding mechanism to prevent atmospheric air from rushing into the drainage device. Instead, syringe needle 38 slowly bleeds atmospheric air into the underwater drainage device to relieve the excess negativity, but prevents too great a volume of atmospheric air from entering the drainage device and destroying the desired negativity. After the excess or high negativity is relieved in the underwater drainage device, spring 20 overcomes atmospheric pressure to return O-ring 32 to the sealing position against housing cap 34. Negative pressure relief valve 10 is then again ready to automatically relieve any excess negativity in the drainage device.

In the preferred embodiment of the present invention, spring 20 is designed to press O-ring 32 against housing cap 34 so long as the negative pressure in the drainage device is greater than −20 cm. of water. However, when the negative pressure is equal to or less than −20 cm. of water, spring 20 is designed to compress due to the force of atmospheric pressure on end member 26 and allow atmospheric air into the drainage device.

Although the invention has been described in detail with respect to an exemplary embodiment thereof, it will be understood by those of ordinary skill in the art that variations and modifications can be effected within the scope and spirit of the invention.

What is claimed is:

1. A device for reducing high negativity within an underwater drainage device comprising, in combination a housing including a syringe needle and having a passageway therethrough to atmosphere, underwater drainage device, a resealable portion in the underwater drainage device which fluidly communicates with the negative pressure therein and which is pierced by said syringe needle, valve means disposed in said passageway to provide a closable passageway from atmosphere through the housing and syringe needle during use, and spring means for urging the valve means to a closed position when the degree of negativity to which the syringe needle is exposed is less than a predetermined value and whereby the valve means opens when the degree of negativity to which the syringe needle is exposed is greater than the predetermined value.

2. A device according to claim 1 wherein the valve means includes a valve housing having an opening to atmosphere in one end thereof and a slidable valve member within said housing.

3. A device according to claim 2 and further including a resilient seal mounted on said slidable valve for sealing the opening to atmosphere.

4. A device for regulating the degree of negativity within an underwater drainage apparatus comprising, in combination, an underwater drainage device, a syringe needle having a passageway therethrough having a needle holder connected thereto, a valve housing having on one end thereof an outwardly extending tubular portion with a passageway therethrough, said tubular portion of the valve housing being frictionally fit within the end portion of the needle holder, an opening to atmosphere in the opposite end of the valve housing, a slidable valve member within the housing, sealing means on the valve member for closing the opening to atmosphere in the valve housing, air passageways formed in the valve member, spring means for urging the valve member to a position wherein the sealing means closes the opening to atmosphere in the valve housing, and a resealable portion in the underwater drainage device which fluidly connects with the negative pressure therein and which is pierced by said syringe needle, said valve member slidable to a position to open the valve when the passageway in the syringe needle is exposed to an atmosphere having a negativity of greater than a predetermined value so that air may pass from atmosphere, through the valve into the passageway in the syringe needle, and into the underwater drainage device to relieve excess negativity therein.

5. A method of reducing high negativity in an underwater drainage apparatus comprising the step of piercing a resealable portion of the apparatus with a syringe needle, providing a valve in communication with the syringe needle, the valve being preset to open a passageway from atmosphere through the syringe needle when the negativity within the underwater drainage apparatus exceeds a predetermined value so that the valve opens to admit sufficient air to the apparatus to bring the negativity within the chamber to the desired level and removing the syringe needle from the resealable portion of the apparatus.

6. A method according to claim 5 wherein the resealable portion of the apparatus comprises the thoracotomy tube.

7. A method according to claim 5 wherein the predetermined negative value at which the valve opens at a negativity within the underwater drainage apparatus of $-20$ cm of water.

* * * * *